United States Patent [19]

Kingsman et al.

[11] Patent Number: 6,096,538
[45] Date of Patent: Aug. 1, 2000

[54] RETROVIRAL VECTORS

[75] Inventors: Alan John Kingsman; Susan Mary Kingsman, both of Islip, United Kingdom; Paula Marie Cannon, South Pasadena, Calif.

[73] Assignee: Oxford Biomedica (UK) Limited, Oxford, United Kingdom

[21] Appl. No.: 08/952,948

[22] PCT Filed: May 22, 1996

[86] PCT No.: PCT/GB96/01230

§ 371 Date: Nov. 19, 1997

§ 102(e) Date: Nov. 19, 1997

[87] PCT Pub. No.: WO96/37623

PCT Pub. Date: Nov. 28, 1996

[30] Foreign Application Priority Data

May 22, 1995 [GB] United Kingdom ............... 9510272

[51] Int. Cl.[7] .................................................. C12N 15/00
[52] U.S. Cl. .................... 435/325; 435/69.1; 435/320.1; 435/455; 424/93.21
[58] Field of Search ................... 435/325, 69.1, 435/320.1, 455; 424/93.21; 536/23.1

[56] References Cited

U.S. PATENT DOCUMENTS

| | | | |
|---|---|---|---|
| 4,738,922 | 4/1988 | Hasetine et al. ........................ | 435/68 |
| 5,665,577 | 9/1997 | Sodroski et al. ........................ | 43/455 |
| 5,672,510 | 9/1997 | Eglitis et al. ........................... | 435/325 |
| 5,693,508 | 12/1997 | Chang ...................................... | 435/455 |
| 5,716,832 | 2/1998 | Barber et al. ............................ | 435/455 |
| 5,747,307 | 5/1998 | Lever et al. ............................. | 435/455 |

FOREIGN PATENT DOCUMENTS

| | | |
|---|---|---|
| 0 759 471 A1 | 2/1997 | European Pat. Off. . |
| WO94/21806 | 9/1994 | WIPO . |
| WO96/14332 | 5/1996 | WIPO . |

OTHER PUBLICATIONS

Soneoka et al., Nucleic Acid Research, vol. 23, 4, 628–633, 1995, p. 9345, 1995.
Crystal, Science, vol. 270:404–410, 1995.
Gunzburg et al. (Molecular Medicine Today, pp. 410–417, 1995).
Hariharan et al. (Nucleic acids Research, vol. 16, No. 19, 1988).

*Primary Examiner*—Scott D. Priebe
*Assistant Examiner*—Dave Trong Nguyen
*Attorney, Agent, or Firm*—Wenderoth, Lind & Ponack, L.L.P.

[57] ABSTRACT

A DNA construct is disclosed which comprises a packagable retroviral genome operably linked to a first promotor, wherein the retroviral genome comprises a 5' long terminal repeat (5' LTR) which includes sequences encoding R and U3 regions and 3' long terminal repeat (3' LTR) which includes sequences encoding R and U3 regions, and wherein at least said R regions of the 5' LTR and 3' LTR are identical to each other and are different from those of the retrovirus on which the retroviral genome is based. The DNA constructs are useful in the production of packaged retroviruses.

36 Claims, 11 Drawing Sheets

Vector DNA

MLV
HIV

Transcription ↓

Viral RNA

Reverse transcription ↓

Proviral DNA

HIV
MLV

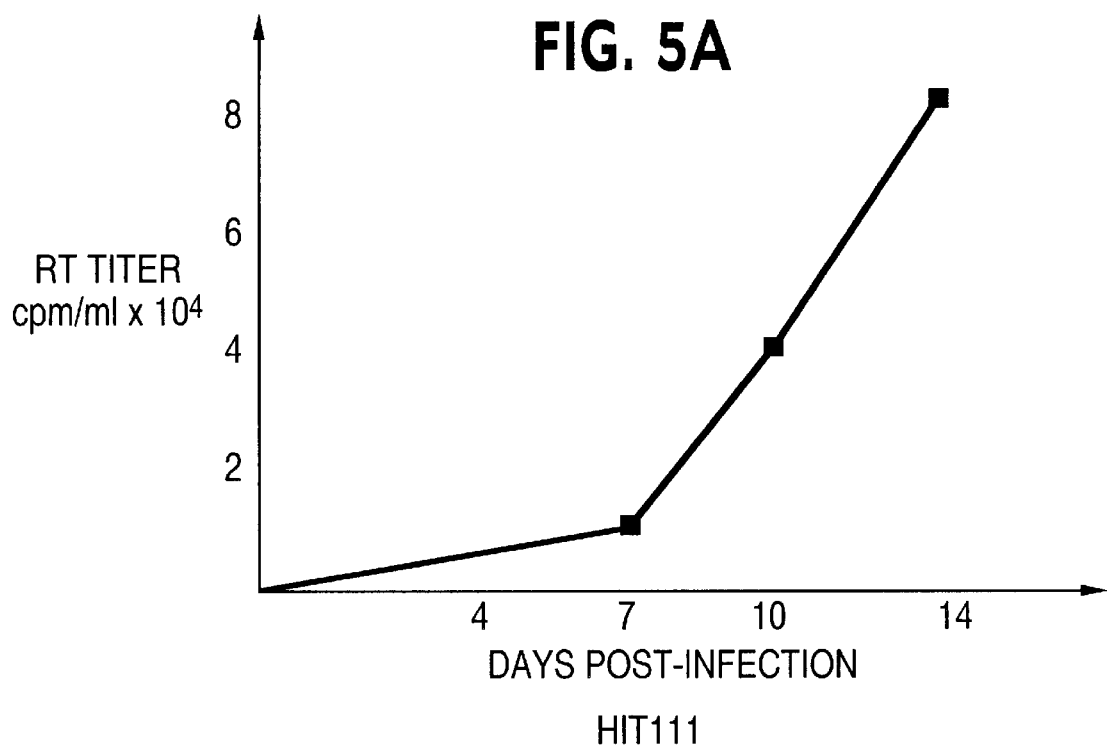
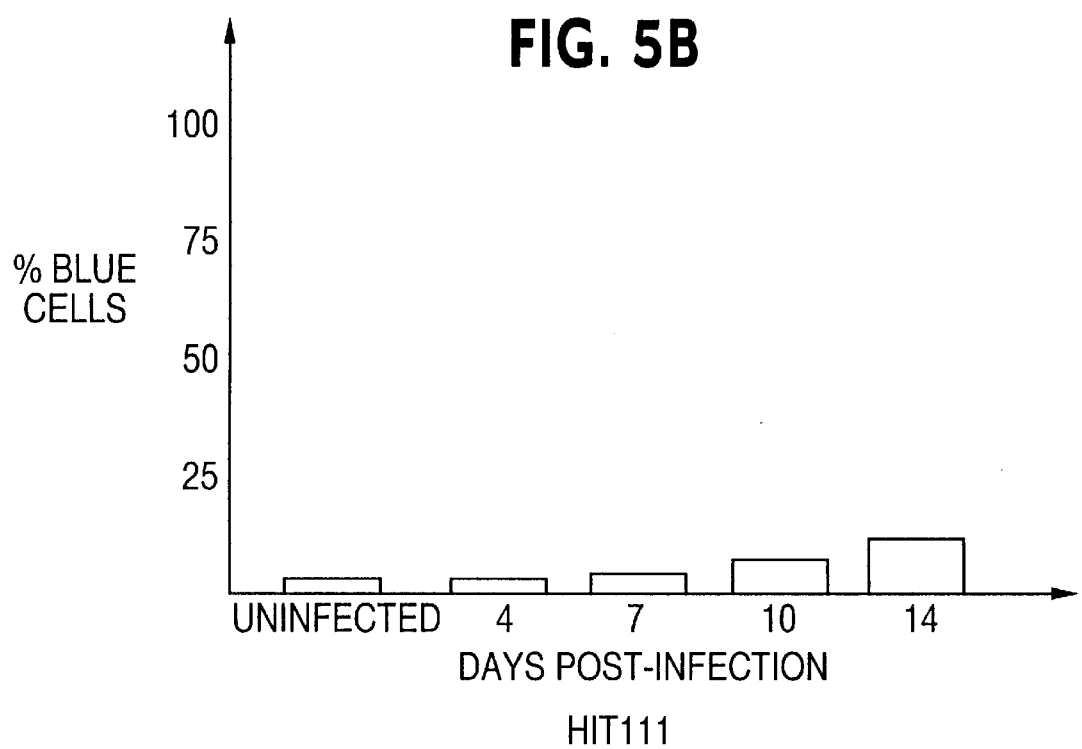

HIT111

TIN414

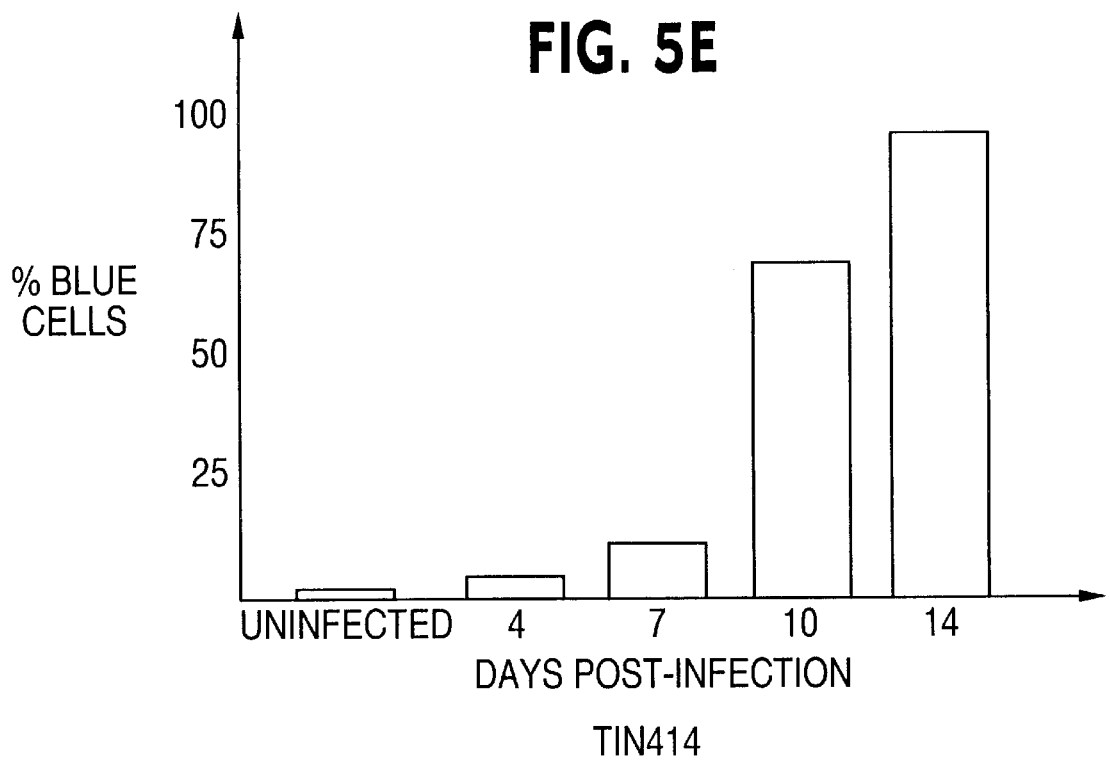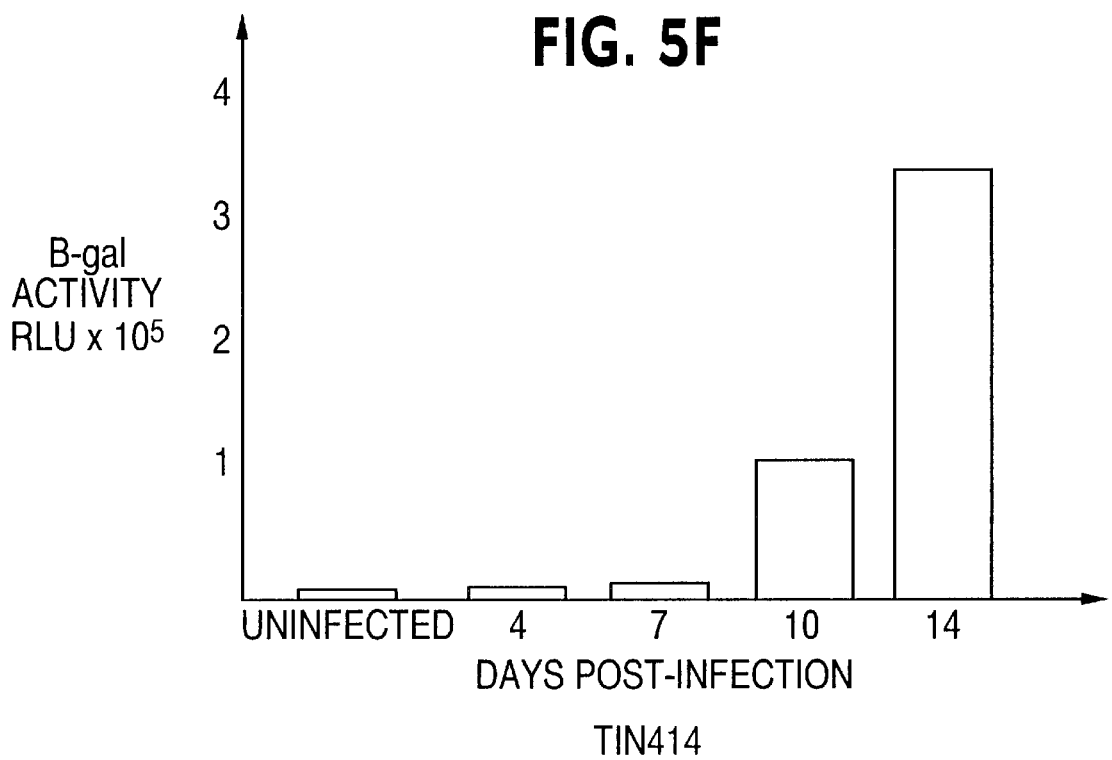

```
                          SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: other nucleic acid
         (A) DESCRIPTION:    /desc = "Synthetic DNA primer"

(xi) SEQUENCE DESCRIPTION: SEQ ID NO: 1:

GCGAGCTAGC TTCGAATCGT GGTCTCGCTG TTCCTTGG                             38

(2) INFORMATION FOR SEQ ID NO: 2:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: other nucleic acid
         (A) DESCRIPTION:    /desc = "Synthetic DNA primer"

(xi) SEQUENCE DESCRIPTION: SEQ ID NO: 2:

GGCCGCTAGC GTTCAGAACT CGTCAGTTCC ACCAC                                35

(2) INFORMATION FOR SEQ ID NO: 3:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION:    /desc = "Synthetic DNA primer"

(xi) SEQUENCE DESCRIPTION: SEQ ID NO: 3:

TTAAGCCTCA ATAAAGCTTG CCTTGAGTGC TTCATC                               36

(2) INFORMATION FOR SEQ ID NO: 4:

(i) SEQUENCE CHARACTERISTICS:
         (A) LENGTH: 34 base pairs
         (B) TYPE: nucleic acid
         (C) STRANDEDNESS: single
```

-continued

```
        (D) TOPOLOGY: linear (ii) MOLECULE TYPE: other nucleic acid
        (A) DESCRIPTION:   /desc = "Synthetic DNA primer"

(xi) SEQUENCE DESCRIPTION: SEQ ID NO: 4:

CGGATGAAGC ACTCAAGGCA AGCTTTATTG AGGC                                        34

(2) INFORMATION FOR SEQ ID NO: 5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Synthetic DNA primer"

(xi) SEQUENCE DESCRIPTION: SEQ ID NO: 5:

CCGCGCTAGC GATATCCTTG ATCTGTGGAT CTACCAC                                     37

(2) INFORMATION FOR SEQ ID NO: 6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Synthetic DNA primer"

(xi) SEQUENCE DESCRIPTION: SEQ ID NO: 6:

GCGAGGGTAC CGTCGACTGC TAGAGATTTT CCACACTGAC                                  40
```

RETROVIRAL VECTORS

This invention relates to retroviral vectors and to DNA constructs encoding RNA genomes for retroviral vectors. In particular it relates to retroviral vectors for gene therapy for treatment or prevention of retrovirus infections, such as HIV.

Despite intensive research efforts, there has been limited success in the development of low molecular weight compounds as treatments for HIV infection and AIDS. Similarly, it seems unlikely that a protective or therapeutic vaccine will be produced in the near future. This situation has led to recent proposals that greater emphasis should be given to biological therapeutics (Lehrman, 1994) and there is currently much interest in the prospect of gene therapy as a clinical approach to HIV-1 infection. Several molecules have been proposed as anti-HIV therapeutics, including ribozymes, trans-dominant proteins, scFv molecules, antisense constructs and TAR and RRE decoys (reviewed in Yu et al. 1994). These molecules are envisaged to act both as therapy against already infected cells and as protective 'intracellular immunisation' (Baltimore, 1988) in uninfected cells. In addition, the use of toxins (suicide genes) or immunological markers has also been proposed as a means of killing infected cells and so reducing the viral load in the patient.

For many of these molecules, it is desirable that expression can be regulated. This is clearly the case for suicide genes, but the constitutive expression of a therapeutic protein may also be undesirable in that it may cause some cellular toxicity or lead to a host immunological response. Furthermore, toxic side effects are also possible from the expression of RNA molecules in cells, including the inappropriate induction of interferon responses. In the case of HIV, the viral LTR promoter itself has the characteristic of being an inducible promoter, directing low basal levels of transcription in the absence of the virally encoded Tat trans-activator protein (Arya et al. 1985). Tat-inducibility is a property of sequences in the U3 region of the LTR and the TAR sequence in the R region (Berkhout and Jeang, 1992). Allowing the HIV LTR to direct expression of a therapeutic gene will therefore limit its expression to those cells infected by HIV. Several groups have already started exploring ways of using this property of the LTR and have demonstrated inducible expression of genes upon HIV infection (Caruso et al. 1992, Brady et al. 1994).

Current strategies to deliver a Tat-inducible therapeutic gene (TITG) by MLV based retroviral vectors place the TITG internally in the vector. A major drawback of placing a second promoter within the retroviral LTR transcriptional unit (either in a sense or antisense orientation) is that it can result in reduced gene expression (Kadesch et al. 1986, Williams et al. 1986, McIvor et al. 1987, Bowtell et al. 1988). This is not suprising as it has been shown that the activity of promoters is often reduced when placed downstream from an active promoter, (Cullen et al. 1984, Emerman and Temin, 1984, Emerman and Temin 1986, Overell et al. 1988) and internal promoters can be unstable in long term culture, even without selection for the vector LTR driven gene (Xu et al. 1989, Li et al. 1992). Furthermore, transcriptional readthrough from an upstream retroviral promoter can also be a problem when expression of the internally placed gene is to be under the control of a regulated promoter, such as the HIV LTR.

Several strategies have been developed for preventing readthrough or interference from the 5' vector promoter. The simplest option to prevent unwanted expression by readthrough is to place the TITG in reverse orientation to the vector LTR (Brady et al. 1994, Liem et al. 1993). However, this configuration can lead to lower levels of transduction or expression (Stuhlman et al. 1989, Poznansky et al. 1991) and may lead to suppression of gene expression by antisense transcripts originating from the vector LTR.

A further possibility is to use a self-inactivating (SIN) vector (Yu et al. 1986). Here, part of the 3' U3 sequences in the vector plasmid are deleted, resulting in a non-functional promoter in the transduced vector. Unfortunately, these vectors give rise to low titers of packaged vector (Hantzopoulos et al. 1989), which is unacceptable for current gene therapy applications.

A third strategy is to clone a promoter-gene cassette into the U3 region of the 3' vector LTR, so that following transduction, the gene and promoter are present in double copies at both LTRs (DC vectors) (Hantzopoulos et al. 1989). Transcription from the upstream unit is less susceptible to interference from the retroviral promoter. However, this configuration necessarily leads to the presence of the promoter-gene cassette at the 3' as well as the 5' end of the vector, where it will still be susceptible to readthrough expression from both the remaining 5' vector LTR and any internal constitutive promoters. The inclusion of both a promoter and the gene into the U3 region may also lead to problems of instability, as lengthening the size of the LTR is associated with decreased stability (Rhode et al. 1987).

There is clearly therefore a need for new and more effective retroviral vectors capable of introducing into a host cell a gene under transcriptional control of a retrovirus regulatory protein-inducible promoter. In particular there is a need for such vectors, which may be for example MLV based vectors, that will allow the exclusive 5' positioning of a TITG without reducing viral titers, that is titers of the packaged vector. In addition the configuration should not significantly interfere with the subsequent regulatory protein-dependent eg. Tat-dependent expression of the gene. Furthermore, and with specific reference to MLV as an example, the introduction of the inducible promoter eg. HIV promoter at the 5' end of an MLV genome must not significantly interfere with the following processes in the MLV life-cycle, which depend on cis-acting sequences of the viral genome:
1. packaging of the vector genome by MLV retroviral cores;
2. reverse transcription of the RNA genome by MLV reverse transcriptase (RV);
3. integration of the DNA copy of the genome by MLV integrase (IN).

The invention therefore provides in one aspect a retroviral vector based on a first retrovirus, said vector comprising a packagable RNA genome capable of being inserted into a host cell genome when in the form of a DNA provirus, said RNA genome comprising sequences which provide in the DNA provirus:

a) a regulated promoter which is inducible by a regulatory factor;
b) a selected gene or genes under transcriptional control of the promoter in a);
wherein the regulated promoter a) is present in the 5' long terminal repeat (LTR) of the provirus in place of the 5' LTR promoter function of the first retrovirus, and the selected gene or genes b) is located between the LTRs.

In another aspect, the invention provides a DNA construct encoding the packagable RNA genome for the retroviral vector described herein, under the control of a promoter. In the DNA construct the selected gene or genes may be present, or be absent in which case the construct has an insertion site at which the selected gene or genes may be inserted into it.

In a further aspect, the invention provides a retroviral vector production system comprising a packaging cell line transfected with a DNA construct as described herein, said system capable of producing retroviral vectors as described herein.

In a still further aspect, the invention provides the use of retroviral vectors as described herein for gene therapy and infected or transduced target cells resulting from such therapy.

The first retrovirus may be MLV, which is the most widely used retroviral vector system and has been used in human gene therapy applications. Other retroviruses may be used instead however, with examples including ASLV, SNV and RSV, all of which have been split into packaging and vector components for retroviral vector production systems.

As will be evident, in order to function as a vector the retroviral vector according to the invention will need to have a reverse transcription system (compatible reverse transcriptase and primer binding sites) and an integration system (compatible integrase and integration sites) allowing conversion to the provirus and integration of the double-stranded DNA into the host cell genome. Additionally, the vector genome will need to contain a packaging signal. These systems and signals are described in more detail below and will generally be provided by the first retrovirus, on which the vector is based. It will be evident also that although the vector according to the invention is based on a particular first retrovirus, this may be a genetically or otherwise (eg. by specific choice of packaging cell system) altered version of the retrovirus. For example, portions of the first retroviral genome not required for its ability to be packaged, undergo reverse transcription and integrate, can be excluded. Also, the vector can be altered eg. by using different env genes to alter the vector host range and cell types infected or transduced.

The regulated promoter allows expression of the selected gene or genes only under certain conditions. In the preferred embodiment described herein, the regulated promoter is inducible by a regulatory protein from a second retrovirus. However, it will be clear that in principle any expression control element that is active only under certain conditions may be employed in a vector according to the invention to enable the conditional expression of a gene or genes encoded by the vector. This could be useful for example for targeting of gene products to particular cell types. The nuclear factor kappa B enhancer is responsive to T-cell activation and could thus be employed to target activated T-cells. Heavy metal induction of a gene could be achieved using components of the metallothionein promoter. Expression control by a steroid hormone may be another useful approach.

The second virus as already discussed may be HIV or any other retrovirus for which it is desirable to provide a regulated gene response and which acts on an inducible promoter. Examples are MMTV and HTLV-1. HIV-1 and HIV-2 are clearly important candidates.

The regulatory factor which induces promoter activity could be any protein produced by the second retrovirus and capable of regulating gene expression via a site on the provirus DNA. For HIV this is preferably Tat but could instead be for instance the Rev protein. Tat acts on the TAR region of R, but also requires sequences in the U3 region to function properly. Certain sections of both U3 and R can be removed while still leaving an effective Tat-responsive element. Deletions in HIV-2 U3 result in promoters with lower basal levels of transcription that still remain responsive to Tat (Brady et al. 1990). Thus, the regulatory protein-inducible promoter, where HIV is the second retrovirus, is preferably the functional portions of both U3 and R from HIV. Alternatively, certain U3 and/or R sequences or portions thereof from other retroviruses, which are responsive to the HIV Tat protein, may be used, for example U3 from RSV linked to R from HIV. Also, U3 from HIV-2 will work with HIV-1 as the second retrovirus.

The selected gene under control of the regulated promoter encodes a gene product which serves a particular purpose, for example it acts as a marker by producing a detectable product or preferably, it is a therapeutic gene whose product is active against infection or disease, in particular against infection by the second retrovirus such as HIV. Therapeutic genes may encode for example an anti-sense RNA, a ribozyme, a transdominant negative mutant of a target protein, a toxin, a conditional toxin, an antigen that induces antibodies or helper T-cells or cytotoxic T-cells, a single chain antibody or a tumour suppressor protein.

Where two or more genes are present and under transcriptional control of the regulated promoter, there may be an internal ribosome entry site (IRES) eg. from picornaviral RNA, to allow both genes to be translated from a single transcript. Retroviruses incorporating IRES sequences have been constructed by others.

A second or further gene may also be present under the control of a separate promoter. The gene may encode for example a selectable marker, or a further therapeutic agent which may be among the therapeutic agents listed above. Expression of this gene may be constitutive; in the case of a selectable marker this may be useful for selecting successfully transfected packaging cells, or packaging cells which are producing particularly high titers of the retroviral vector. Alternatively or additionally, the selectable marker may be useful for selecting cells which have been successfully infected with the retroviral vector and have the provirus integrated into their own genome. One way of performing gene therapy is to extract cells from a patient, infect the extracted cells with a retroviral vector and reintroduce the cells back into the patient. A selectable marker may be used to provide a means for enriching for infected or transduced cells or positively selecting for only those cells which have been infected or transduced, before reintroducing the cells into the patient. This procedure may increase the chances of success of the therapy. Selectable markers may be for instance drug resistance genes, metabolic enzyme genes, or any other selectable markers known in the art.

It will be understood that there may be more than one constitutively expressed gene in addition to the one or more regulated genes.

However, it will be evident that for many gene therapy applications of retroviral vectors, selection for expression of a marker gene may not be possible or necessary. Indeed expression of a selection marker, while convenient for in vitro studies, could be deleterious in vivo because of the inappropriate induction of cytotoxic T lymphocytes (CTLs) directed against the foreign marker protein. Also, it is possible that for in vivo applications, vectors without any internal promoters will be preferable. The presence of internal promoters can affect for example the transduction titres obtainable from a packaging cell line and the stability of the integrated vector. Thus, single-transcription unit TIN vectors, which may be bi-cistronic or poly-cistronic, coding for one or two or more anti-HIV genes, may be the preferred vector design for use in vivo.

The DNA construct according to the invention which encodes the packagable RNA genome preferably comprises a promoter originating from a source other than the first or second retrovirus. Particularly preferred are strong promoters such as the CMV promoter which give rise to a high level of expression of the vector RNA in the producer cell line.

The invention will now be further described with the help of the accompanying drawings in which:

FIG. 1 shows example configurations of vectors according to the invention:
(a) single Tat-inducible transcription unit with single therapeutic gene;
(b) Tat-inducible transcription unit with conditional toxin and constitutive promoter (SV40) for drug selection marker or second therapeutic gene;
(c) single Tat-inducible transcription unit with two therapeutic genes and IRES; and
(d) single Tat-inducible transcription unit with two therapeutic genes, one being ribozyme.

Figure 1A:
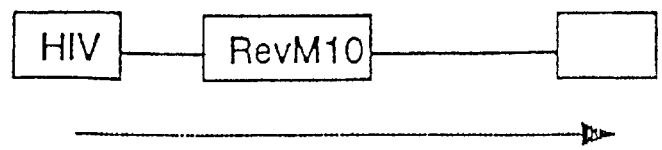
Figure 1B:
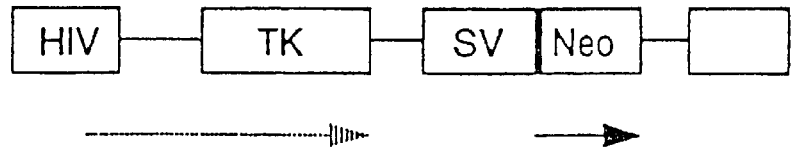
Figure 1C:
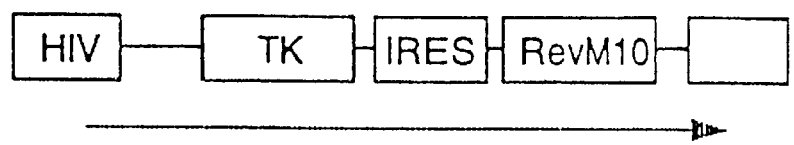
Figure 1D:
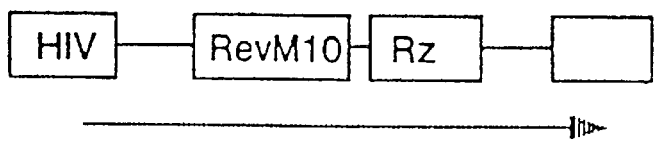
Figure 2A:
FIGS. 2A and 2B show (A) the principle of MLV-based Tat-inducible vectors according to the invention and (B) pTIN414.
Figure 2A:
Figure 2A:
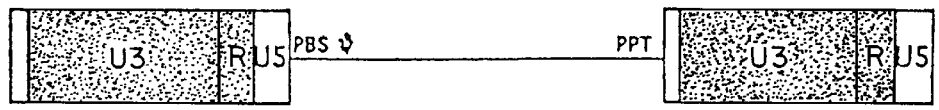
Figure 2B:
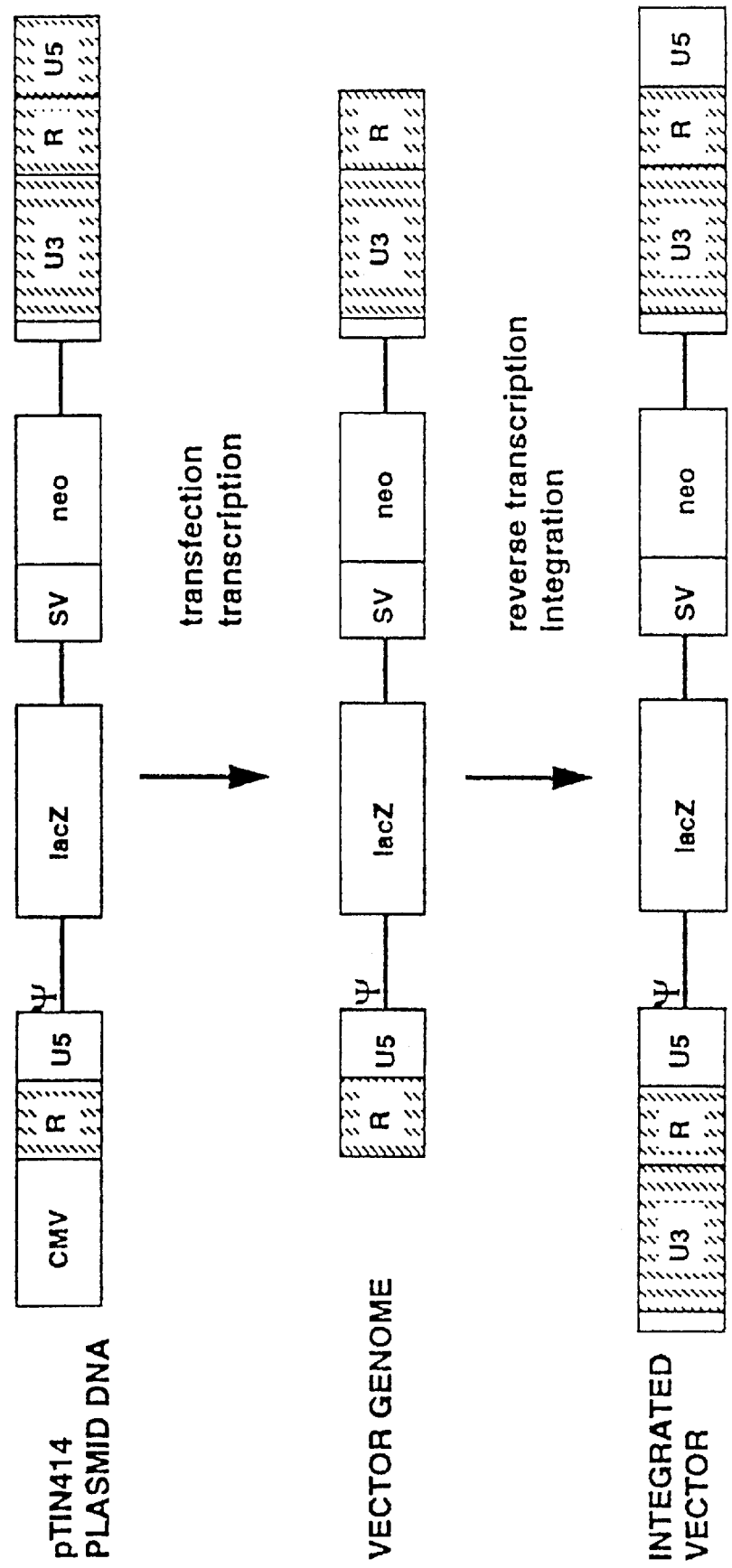

FIG. 2A, which gives the specific example of a vector comprising MLV and HIV, shows the elements from which a vector according to the invention may be constructed. FIG. 2A shows a packagable RNA genome comprising from the 5' end at least the functional part of the R region of a second retrovirus, all or a functional part of a U5 region of a first retrovirus, the functional primer binding site of the first retrovirus for first strand reverse transcription, the functional RNA packaging sites of the first retrovirus, the functional primer binding site of the first retrovirus for second strand reverse transcription, a site at which therapeutic genes might be inserted in the DNA copy, a short (10–100 nucleotides) sequence recognised by the integration system of the first retrovirus, all or a substantial part of the U3 region of the second retrovirus and the R region of the second retrovirus corresponding to the R region at the 5' end.

FIG. 2A further shows the integrated provirus resulting from reverse transcription and integration of the vector, the provirus having the following composition reading 5' to 3' on the sense strand a short sequence (10–100 nucleotides from the first retrovirus which is recognised by the integration system of the first retrovirus, all or a substantial part of the U3 region of the second retrovirus, a functional part of the R region of the second retrovirus, all or a functional part of the U5 region of the first retrovirus which is recognised by the integration system of the first retrovirus, functional packaging and primer binding sites of the first retrovirus, a site at which therapeutic genes may be inserted such that they are under the control of the LTR promoter of the second retrovirus, a functional second strand synthesis primer site from the first retrovirus, a short sequence (10–100 nucleotides) from the first retrovirus that is recognised by the integration system of the first retrovirus this short sequence being identical to the previous short sequence, all or a substantial part of the U3 region of the second retrovirus this component being identical to the previous U3 region, a functional part of the R region of the second retrovirus this component being identical to the previous R region, all or a functional part of the U5 region of the first retrovirus which is recognised by the integration system of the first retrovirus.

We have constructed a novel series of MLV based Tat-inducible (TIN) vectors that, following transduction, contain a Tat-inducible promoter as the 5' vector LTR. TIN vectors contain features predicted to be required for efficient packaging, reverse transcription and integration of the vector genome by the MLV machinery. The hybrid HIV-1/MSV 5' LTR created during reverse transcription has the characteristics of an HIV-1 promoter, directing low levels of expression in human cells in the absence of Tat, but being highly induced following transfection of a Tat-expression plasmid or infection by HIV-1. We have data demonstrating that transduced TIN vectors retain their ability to be highly induced following HIV-1 infection for at least six months. In addition, to facilitate the production of high levels of vector genomes in the producer cells (standard MLV packaging lines or our transient transfection system (Soneoka et al. 1995)), we have designed the packagable vector transcript to be driven from the CMV promoter rather than the natural vector MLV LTR.

Several configurations of these vectors are envisaged (FIG. 1). The simplest of these vectors allow the exclusive expression of therapeutic and or selectable genes from the HIV LTR (a, c and d). We have also constructed a series of two promoter vectors that allow Tat-inducible expression of the 5' gene and constitutive expression of a 3' gene (b). The two promoter TIN vectors will allow, for example, the selection of transduced cells from a constitutively expressed drug resistance gene and the Tat inducible expression of a therapeutic gene upon HIV infection. Alternatively, these vectors can be used to mount a two-stage attack on HIV, allowing both the constitutive expression of one anti-HIV molecule and the Tat-inducible expression of a second gene. An example of such a use would be the constitutive expression of a trans-dominant protein and the 'last resort' expression of a suicide gene if an infection takes hold in the cell. As well as using multiple transcription units in the TIN vector, it is possible (c) to use the single HIV LTR configuration but with multiple translation units by using an internal ribosome entry sequence (IRES) (Adam et al. 1991). It will also be possible within a single Tat-inducible transcript to incorporate additional anti-HIV components in the untranslated regions of the mRNA, for example ribozyme sequences (d). In FIG. 1, the elements of the vectors are represented as follows: HIV-Tat-inducible HIV promoter; TK-thymidine kinase; SV-SV40 promoter; Neo-bacterial neomycin resistance gene; IRES-internal ribosome entry sequence; Rz-ribozyme.

We also predict that the low basal level of transcription from the HIV LTR promoter in the absence of Tat will reduce problems of interference with any downstream constitutive promoters, facilitating stable expression of the constitutive gene in transduced cells. The inactivity of the HIV promoter in the absence of Tat may also be an important safety feature of these vectors, minimising the risk of inappropriate transcription of downstream cellular genes adjacent to the integrated vector.

The clear advantage of this system is the achievement of HIV control of gene expression from a simple transcription unit which can be transduced by the standard MLV-based vector technology. The combination of components required to produce this system has not been assembled before.

COMPONENTS OF MLV BASED TAT-INDUCIBLE (TIN) VECTORS

We have constructed a series of vectors that are packagable by standard MLV components, can be reverse transcribed and integrated by the MLV machinery following infection or transduction of a cell, and will allow Tat-inducible expression of a therapeutic gene from the transduced vector. The basic components of such a vector are as follows (FIG. 2):

1. Tat-inducibility.

The Tat-inducibility of the HIV LTR promoter is a property of sequences in the U3 region of the promoter and also the TAR element in R (Berkhout and Jeang, 1992). In addition, some other promoters, including the U3 regions from HIV-2 and RSV can substitute for the HIV-1 U3 regions to allow Tat transactivation (Liu et al. 1994). In order for the U3 element to appear in the 5' LTR following reverse transcription, it must be present in the 3' LTR of the viral RNA. The vector therefore contains the HIV U3 and R sequences at the 5' LTR.

2. Reverse Transcription.

MLV RT initiates reverse transcription at the primer binding site (PBS). This initial (−) strand synthesis extends into U5 and R sequences, forming the first 'strong stop' DNA strand. The RNAseH moiety of RT then degrades the RNA in this hybrid, allowing the exposed DNA to hybridise with the homologous R region in the 3' LTR of the provirus. The homology between the 5' and 3' R regions enables the polymerase to switch strands and continue synthesis along the (−) strand from the 3' LTR. (+) strand DNA synthesis is primed by the selective retention of an RNA fragment at the polypurine tract after RNAse degradation of the genomic RNA strand (reviewed in Katz and Skalka, 1994). The minimum requirements for MLV pol directed reverse transcription contained in the vector are therefore the PBS to initiate (−) strand DNA synthesis, the PPT to initiate (+) strand DNA synthesis and identical 5' and 3' R sequences to allow the first template switch. The requirement for identical R sequences is met by having HIV R sequences in both 5' and 3' LTRs. In addition, as there is evidence to suggest that secondary structures in the 5' U5 region are also important for the initiation of reverse transcription (Cobrink et al. 1991), we have kept the MLV U5 sequences in the 5' LTR. The 3' U5 sequences do not appear in the genomic RNA transcript; however, to ensure correct termination at the 3' is R/U5 border during genomic transcription, we will use the HIV U5 region in the 3' LTR.

3. Integration.

The termini of the reverse-transcribed molecule contain short, sometimes imperfect, inverted repeats of 2–23 bp, which the retroviral integrase recognises (reviewed in Katz and Skalka, 1994). For MLV, it has been demonstrated that only 9 bases at the end of a linear model substrate are sufficient for almost wild-type levels of integration in an in vitro integration assay system (Bushman and Craigie, 1990). These sequences are derived from the ends of the 3'U3 region and the 5'U5 region in the vector. This requirement is met by the vector containing 36 bases of MLV sequence at the 5' end of the 3' U3 and the whole of the MLV 5' U5 region.

4. Packaging Components.

Efficient packaging of a vector genome into a retroviral particle is dependent on a number of cis-acting sequences (reviewed in Linial and Miller, 1990). The most important sequence is the packaging signal, a highly structured region of RNA at the 5' region of the genome. In addition, other regions of the genome have been found to increase the efficiency of packaging, including sequences in gag p15. This region is included in standard MLV retroviral vectors, such as LXSN (Miller and Rosman, 1989) and is also preserved in our constructs.

5. High Titer Retrovirus Stocks following Transient Transfection.

We have recently devised a system for the rapid production of high titer retroviral vectors (1 $0^7$/ml) by transient transfection (Soneoka et al. 1995). A key feature of this system is that the powerful CMV promoter drives high level expresssion of the vector RNA in the producer cell line and is positioned so that the transcription start site of the vector RNA is exactly the same as the normal LTR-directed start site. To achieve this, we have placed the CMV promoter up to its transcriptional start site adjacent to the start of the HIV R region in the 5' LTR. This principle could be applied to other heterologous promoters, as long as the integrity of the retroviral transcription unit is maintained.

This system has been described for hybrid MLV-HIV vectors, but the same principle can be applied to other combinations of retroviruses, where one retrovirus is donating the cis-acting sequences required by its own packaging components provided in trans (e.g. SNV, RSV. ASLV etc.) and the other retrovirus is used because of the property of conditional expression of its LTR promoter. Further examples of such retroviral promoters are the HTLV-1 promoter (dependent on Tax protein) and the steroid-hormone inducibile MMTV LTR (reviewed in Majors, 1990). The use of HTLV-1 LTR, for example, to direct expression of a suicide gene could find applications as a treatment for adult T-cell leukemia.

EXAMPLES

Example 1

CONSTRUCTION DETAILS

Figure 4:
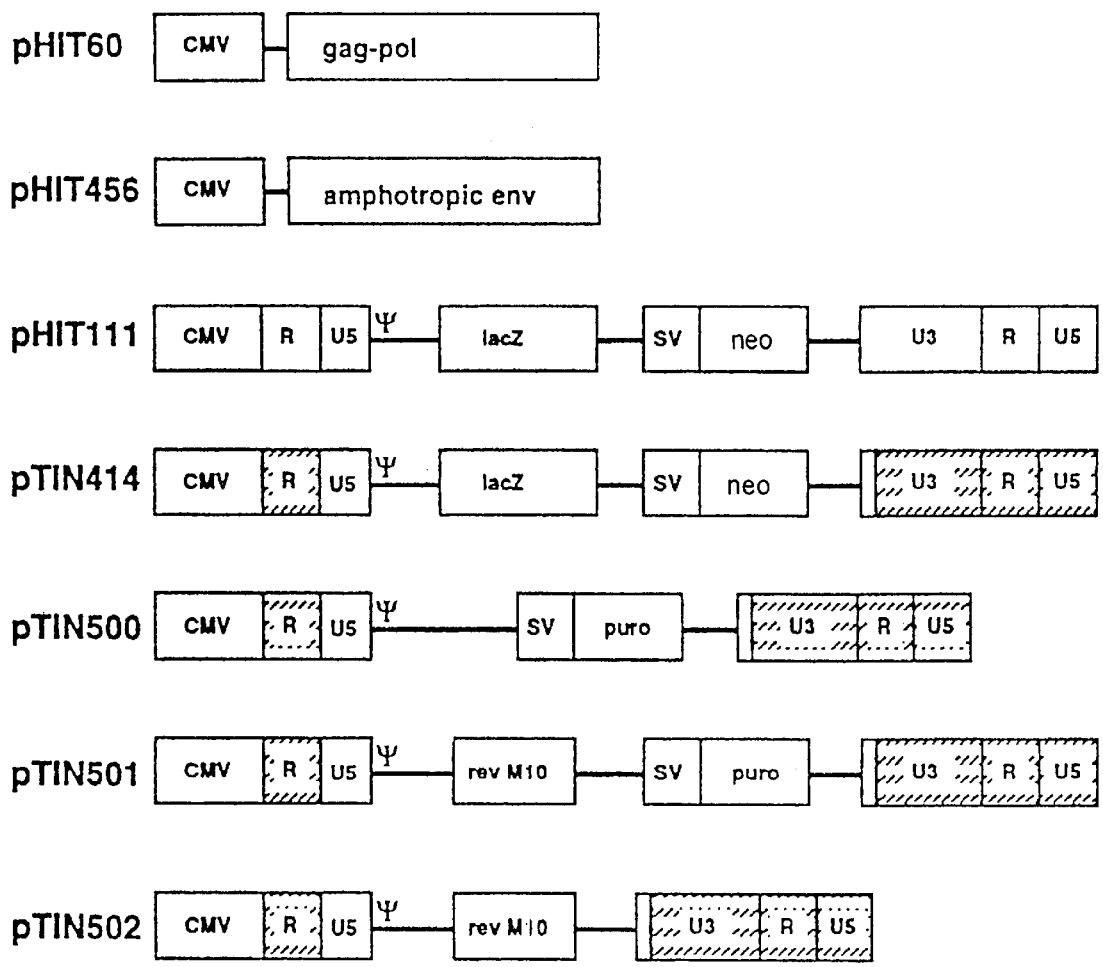
FIG. 4 shows various retroviral packaging components and vectors used in the Examples.

The various retroviral packaging components and vectors used in these Examples are shown in FIG. 4. Plasmid pHIT60 is a MLV gag-pol expression plasmid (Soneoka et al 1995). pHIT456 is an MLV amphotropic envelope expression plasmid derived from plasmid SV-A-MLV-env (Page et al. 1990) and is essentially the same as the ecotropic expression construct pHIT123 (Soneoka et al 1995). Retroviral vector pHIT111 (Soneoka et al. 1995) is a derivative of LZSN (Adam et al. 1991) and pTIN414 is the TIN vector equivalent. Subsequent TIN vectors were derived from pTIN414 by replacement of internal sequences between unique SpeI and NheI sites. The SpeI site is located within the non-translated gag coding region upstream of the lacZ gene and the Nhe I site is in the 3' U3 region at the junction of the MLV and HIV-1 sequences. Plasmid pTIN500 contains the SpeI—NheI internal fragment from pBABEpuro. Vector pTIN501 contains the RevM10 coding sequence, amplified from plasmid pM10 (Malin et al. 1989) using PCR primers incorporating flanking EcoRI sites and inserted into the unique EcoRI cloning site of pTIN500. pTIN502 was created by removing the SV40 promoter and puromycin (puro) resistance gene from pTIN501 using AccI sites that flank this cassette.

Figure 3A:
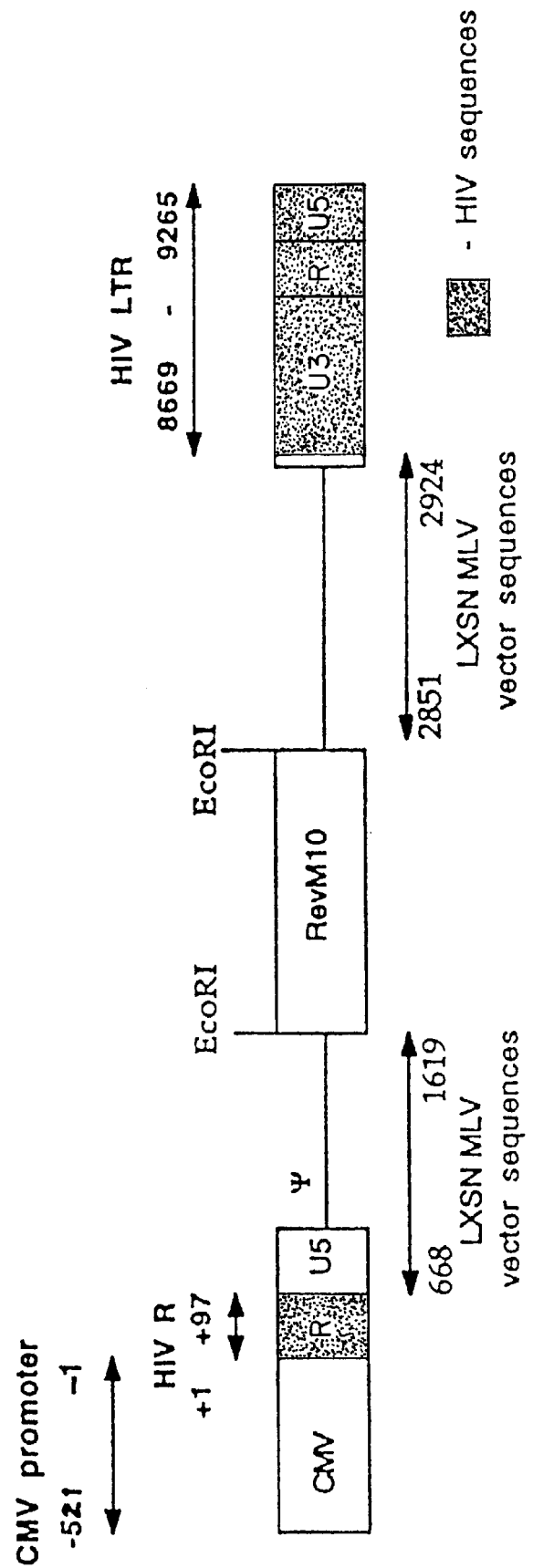
FIGS. 3A and 3B show specific prototype vectors pTIN502 and pTIN414 according to the invention.
Figure 3B:
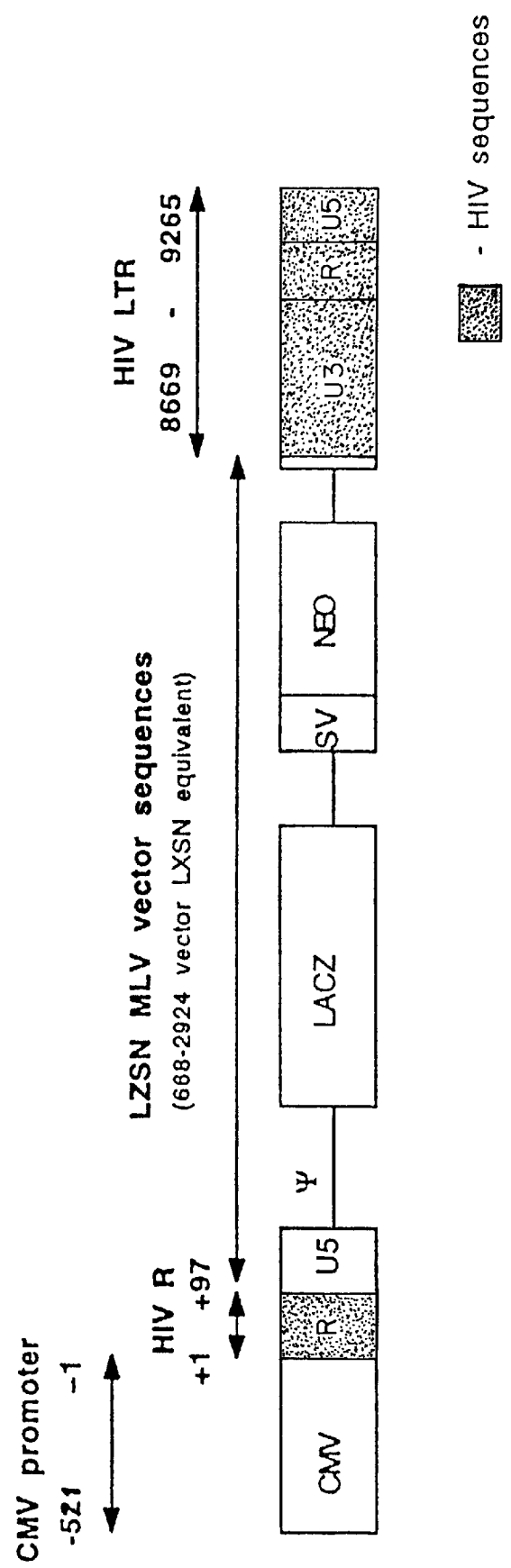

Two of the prototype TIN vectors are shown in FIG. 3. FIG. 3A shows a simple one gene TIN vector, TIN502, expressing the trans-dominant Rev protein RevM1 (Malim et al. 1989). FIG. 3B shows a two promoter vector TIN414 which constitutively expresses neomycin resistance from an internal SV40 promoter and has LacZ expression under control of the HIV LTR. The detailed construction of TIN414 is given below as an example. In FIGS. 3A and 3B, the numbering of HIV-1 sequences is according to Los Alamos data base convertion for HXB2. MLV derived sequences are from (A) vector LXSN (Gerbank accession no. M28248); and (B) vector LZSN (Adam et al. 1991), numbered according to vector LXSN designation. Rev M10 in (A) was amplified from plasmid pM10 (Malin et al. 1989) using primers containing EcoR1 restriction sites.

Detailed Construction of TIN414.

The co-ordinates of the sequences derived from the CMV promoter, the MLV vector LZSN (Adam et al. 1991) and the HIV-1 proviral clone WI3 (Kim et al. 1989) are indicated. The molecule was created using standard recombinant DNA techniques and in addition, recombinant PCR to create exact junctions between the different parts of the molecule (Higuchi 1990). Specifically 1. Construction of the 5' CMV Driven LTR Plasmid pPE611 (Braddock et al. 1989) contains the human CMV promoter (from −521 to +1) joined exactly to the start of the HIV-1 R region (co-ordinates +1 to +80). An Xbal—BamHl fragment from this plasmid was ligated into the cloning vector pBluescript (Stratagene) to give plasmid pRV404. A PCR amplification was performed using plasmid pLNSX as the template, using primers 5'-gcgagctagcttcgaatcgtggtctcgctgttccttgg-3'-[SEQ ID NO: 1] and 5'ggccgctagcgttcagaactcgtcagttccaccac-3' [SEQ ID NO: 2]. The PCR product so generated was digested with NheI and ligated into pRV404 at its NheI site to give plasmid pRV405. Two oligonucleotides of sequence 5'-ttaagcctcaataaagcttgccttgagtgcttcatc-3' [SEQ ID NO: 3] and 5'-cggatgaagcactcaaggcaagctttattgaggc-3' [SEQ ID NO: 4] were annealed together to create a short duplex containing single stranded regions at either end corresponding to the overhangs present on Aflll and BstBI restriction fragments. This molecule was ligated into plasmid pRV405 cut with AflIII and BstBI, to give plasmid pRV406.

2. Construction of the 3' LTR

A HindIII—XbaI fragment from pLNSX was ligated into the cloning vector pSP72 to give plasmid pRV400. Plasmid pBX+contains a BamHI—XbaI fragment from W13 containing the whole 3' LTR from the HIV-1 genome. PCR amplification was performed on pBX+using primers 5'-ccgcgctagcgatatccttgatctgtggatctaccac-3' [SEQ ID NO: 5] and 5'gcgagggtaccgtcgactgctagagattttccacactgac-3' [SEQ ID NO: 6]. The PCR product was digested with KpnI and NheI and ligated into plasmid pRV400 digested with KpnI and NheI, to give plasmid pRV401. The ClaI—KpnI fragment of pRV401 was ligated into pBluescript digested with ClaI and KpnI, to give plasmid pRV408.

3. Addition of Internal Sequences.

A SacII—SpeI fragment from pRV406 was ligated into plasmid pRV408 to create plasmid pRV412. The SpeI—NheI fragment from pRV412 was replaced with the SpeI—NheI fragment from LZSN to give vector pTIN414.

Example 2

CHARACTERISATION

1. Vector TIN414 is Efficiently Transduced by Standard MLV Components.

Retoviral vector stocks were produced by transient transfection of 293T cells according to our previously published protocol (Soneoka et al. 1995). MLV packaging components are provided in trans on two plasmid components - a gag-pol expression plasmid (pHIT60) and an amphotropic or ecotrophic envelope construct (pHIT456 or pHIT123 respectively). The vector genome component was either a standard MLV vector (pHIT111) or the equivalent TIN vector, pTIN414. The culture supernatants were harvested 48 hours after transfection, filtered through a 0.45 μm filter and used to transduce target cells in the presence of 8 μg/ml polybrene for four hours, followed by the addition of fresh media. Virus stocks generated 48 hours after transfection were used to infect either NIH3T3 cells (ecotrophic envelope) or HeLa cells (amphotropic envelope) and stably transduced colonies selected by G418 (0.4 mg/ml). Titers of each retrovirus stock were calculated after 10 days selection as described in Soneoka et al. 1995. (Table 1). From these data it can be seen that vector TIN414 is just as efficiently transduced as the related MLV vector HIT111. This confirms that the TIN vector constructs are efficiently packaged, reverse transcribed and integrated by MLV.

2. LacZ Expression from Transduced Vector TIN414 is Tat Inducible.

Populations of G418 resistant HeLa and NIH3T3 cells transduced with vectors pHIT111 or pTIN414 were produced as described above and designated HeLa-111, 3T3–414 etc. The populations were fully resistant to G418, due to the expression of Neomycin resistance from an internal SV40 promoter. Levels of beta-galactosidase activity were measured in all four populations following transfection with either a Tat expression plasmid or a control CMV vector plasmid. The results, shown in Table 2, confirm that the levels of beta-galactosidase activity from the TIN414 HIV LTR promoter in the absence of Tat are low, but that expression is greatly increased by Tat in HeLa cells. As expected, Tat had very little effect on HIV LTR activity in the rodent NIH3T3 cell line. This represents a model system for the Tat-mediated induction of an anti-HIV therapeutic gene.

3. LacZ Expression from Vector TIN414 is Inducible by HIV Infection.

Figure 5C:
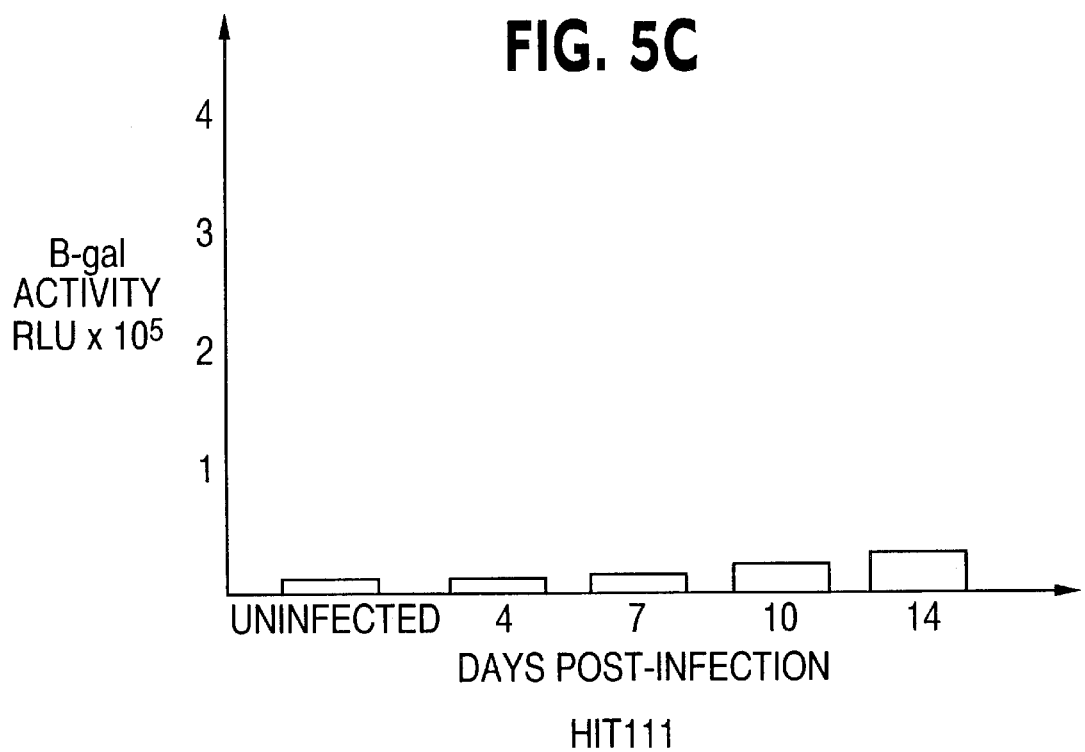
FIG. 5 shows results from Example 2.3: HIV-1 infection induces expression from the TIN vector 5' LTR.
Figure 5D:
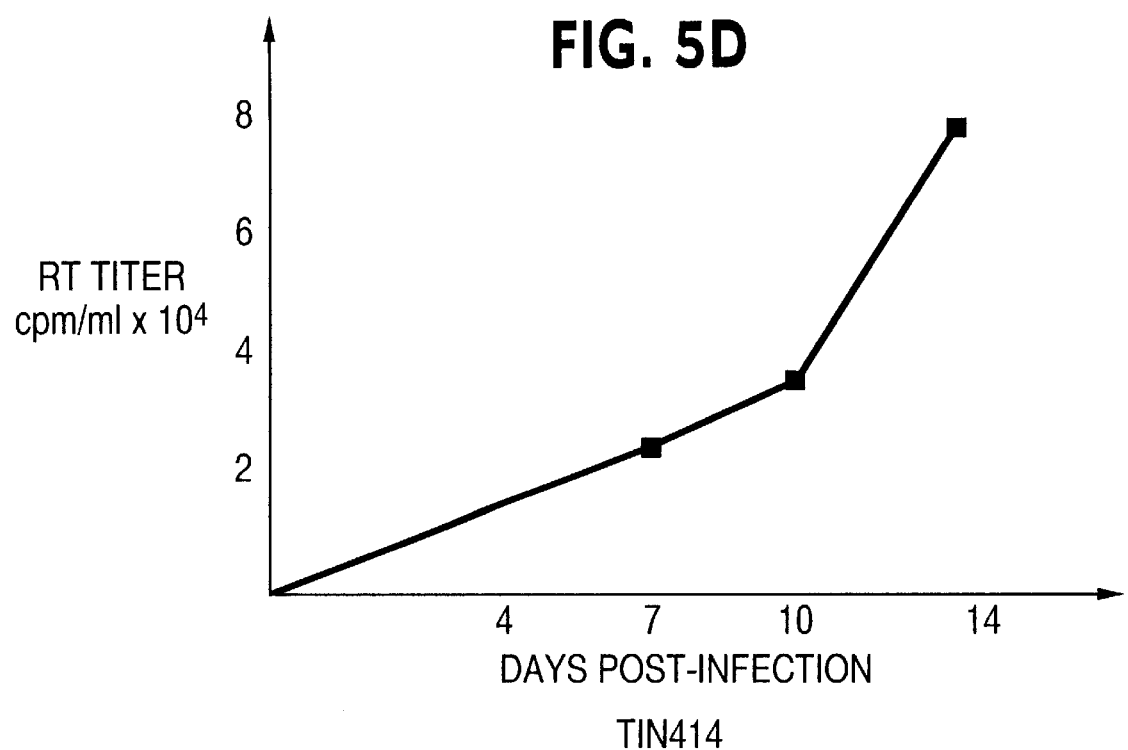

PTIN414, pHIT60 and pHIT456 or pHIT111, pHIT60 and pHIT456 were transfected into 293T cells as above. The supernatants were used to transduce the promonocytic cell line U937 with pHIT111 (FIGS. 5A–C) or pTIN414 (FIGS. 5D–F). U937 cells are CD4+ and can be efficiently infected by HIV-1. Neomycin resistant populations were selected with G418 for fourteen days to give a fully transduced population and analysed for LacZ expression using standard beta-galactosidase staining procedures (FIG. 5B and 5E). The U937-HIT111 population displayed high levels of lacZ expression (approximately 2.5% of the cells staining visibly blue), whereas the U937-TIN414 population did not (<0.1% cells visibly blue). 2×10$^6$ cells from each population were pelleted and infected with HIV-1 by resuspending the cells in 1 ml of HIV$_{IIIB}$ virus (at 1 μg/mi p24) containing 6×10$^5$ TCID50. Following incubation for 2 hours at 37° C., an additional 5 ml of media was added to the cells and the cells then incubated for four days to allow viral spread. Samples of the supernatant were taken every three to four days and assayed for reverse transcriptase (RT) activity using a Quant-T RT kit (Amersham) as described (Cannon et al. 1994) (FIG. 5A and D). In addition, samples of the cells were taken at various time-points and assayed for β-galactosidase expression using both X-gal staining of fixed cells (FIG. 5B and E) and a luminescent assay for enzyme activity in cell extracts (FIG. 5C and F-RLU is relative light units). β-galactosidase expression in the U937-HIT111 population remained constant at around 2.5% cells appearing blue until day 10 post-infection, when an increase was observed to a maximum of 11% at day 14. In contrast, β-galactosidase expression in the U937-TIN414 population was highly induced following HIV-1 infection, rising from <0.1% of the cells staining blue in the uninfected population to 96% at day 14 post-infection and reflecting the spread of the HIV-1 infection in the population. β-galactosidase activity monitored in the luminescent assay increased in a similar manner. Comparisons of the amount of enzyme activity at day 14 gave an infected:uninfected ratio of 1.7 for the U937-HIT111 population, whereas the U937-TIN414 population showed a 102-fold increase in the infected cells. These data clearly demonstrate induction of expression from the TIN vector 5' LTR in TIN414 following HIV-1 infection. When IacZ is replaced with an anti-HIV gene then the anti-HIV gene would also be induced when the cell was infected by HIV.

Figure 6A:
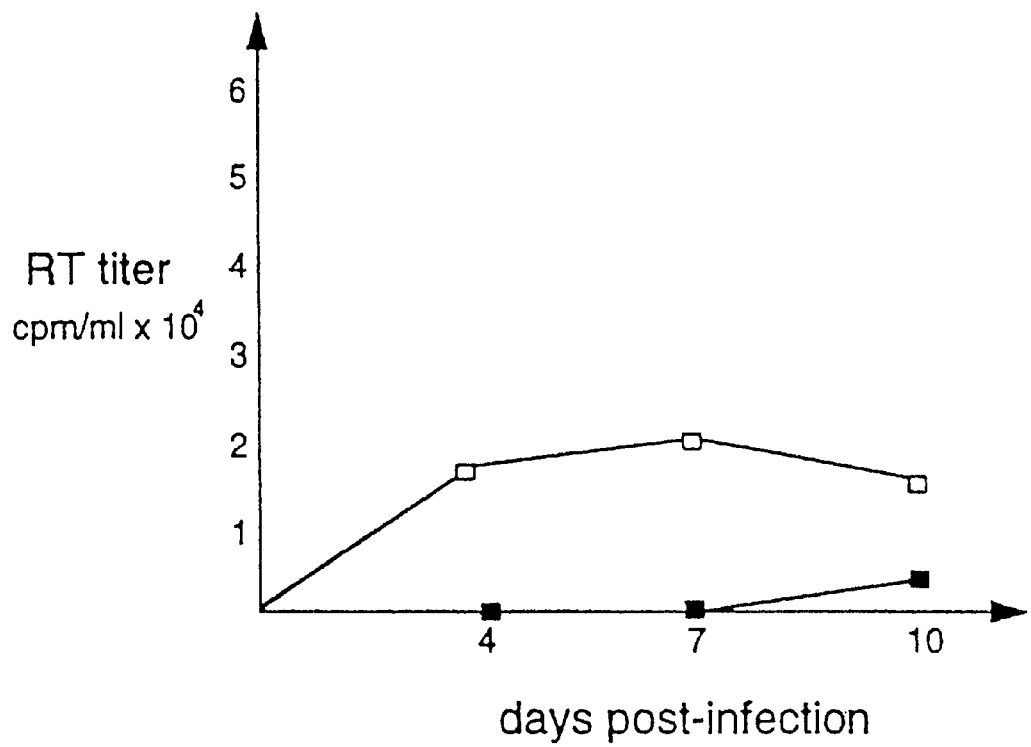
FIG. 6 shows results from Example 2.4: an anti-HIV TIN vector protects from HIV-1 infection.
Figure 6B:
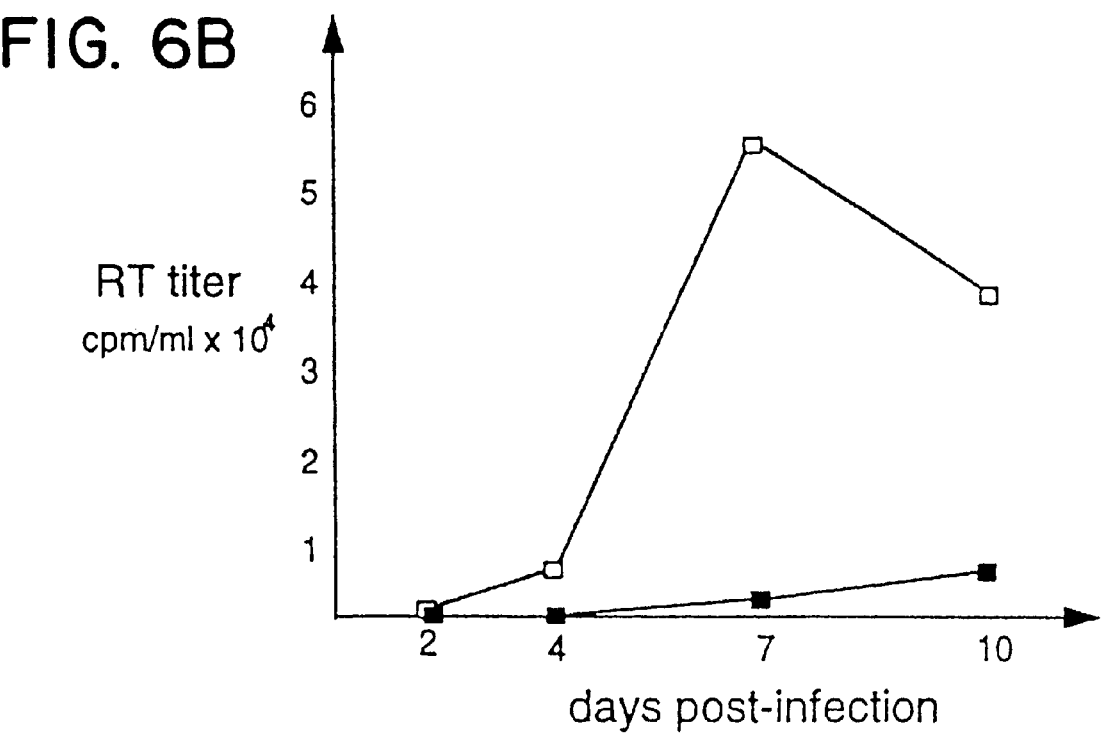

4. Protection from HIV-1 Infection by an Anti-HIV TIN Vector.

pTIN501 contains the trans-dominant mutant protein RevM10 (Malin et al. 1989) driven from the tat-inducible promoter, together with an internal drug selection cassette (puromycin). RevM10 has previously been shown to protect cells from HIV-1 infection, both when expressed constitutively or under the control of an HIV-1 LTR promoter. Following transduction of pTIN501, RevM10 expression will be under the control of the Tat-inducible 5' vector LTR. pTIN501 (■) and the parental vector pTIN500 (□) were transduced into U937 cells and stable populations generated by selection in puromycin (Sigma) for 10 days at 1.5 μg/ml. $2 \times 10^6$ cells from each population were infected with either 20 μl (A) or 200 μl (B) of an HIV-$1_{111}$B viral stock at $5 \times 10^6$ $TCID_{50}$ per ml and the infection was monitored by assaying the culture supernatant every three days for RT activity. The rate of viral replication was markedly reduced in the TIN501 population relative to the TIN500 population (FIG. 6.), due to the induction of the anti-viral RevM10 protein in those cells. This demonstrates a protective effect of RevM10 in this Tat-inducible configuration. We observed no significant protection of TIN500 transduced cells relative to the non-transduced U937 population (data not shown), despite the presence of potential Tat decoys in the TIN vector LTRs.

5. Single Transcription unit TIN Vectors.

Figure 7A:
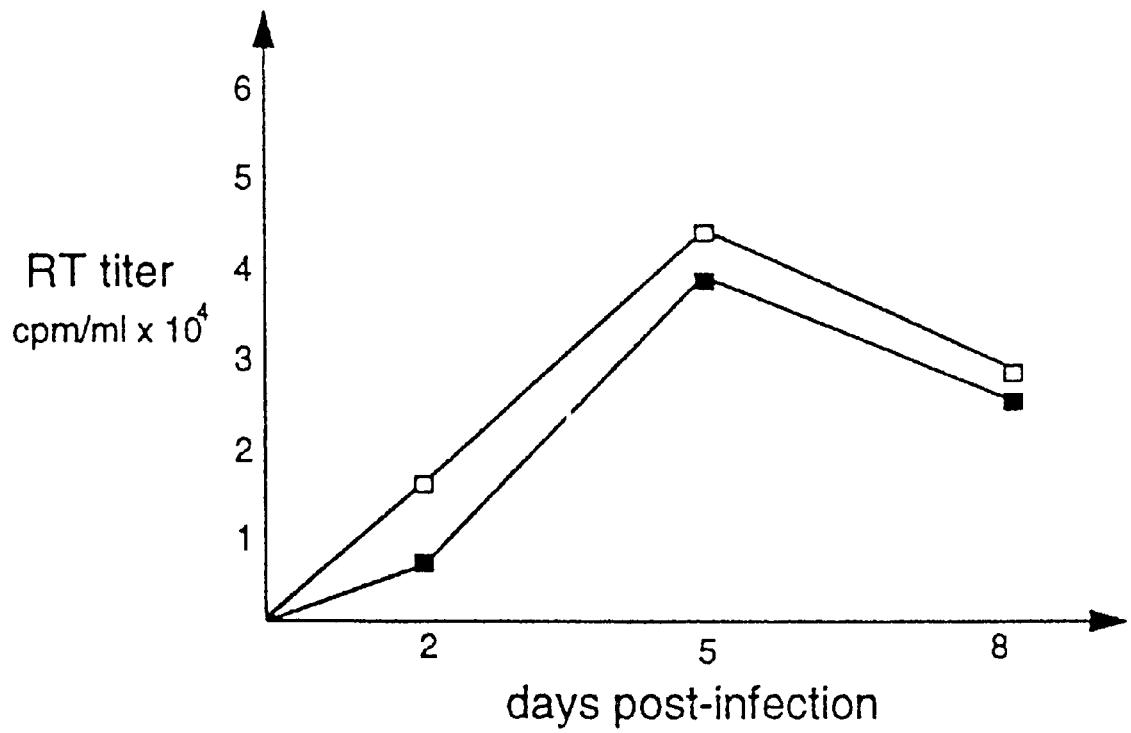
FIG. 7 shows results from Example 2.5: protection from HIV-1 infection by a single transcription unit TIN vector.
Figure 7B:
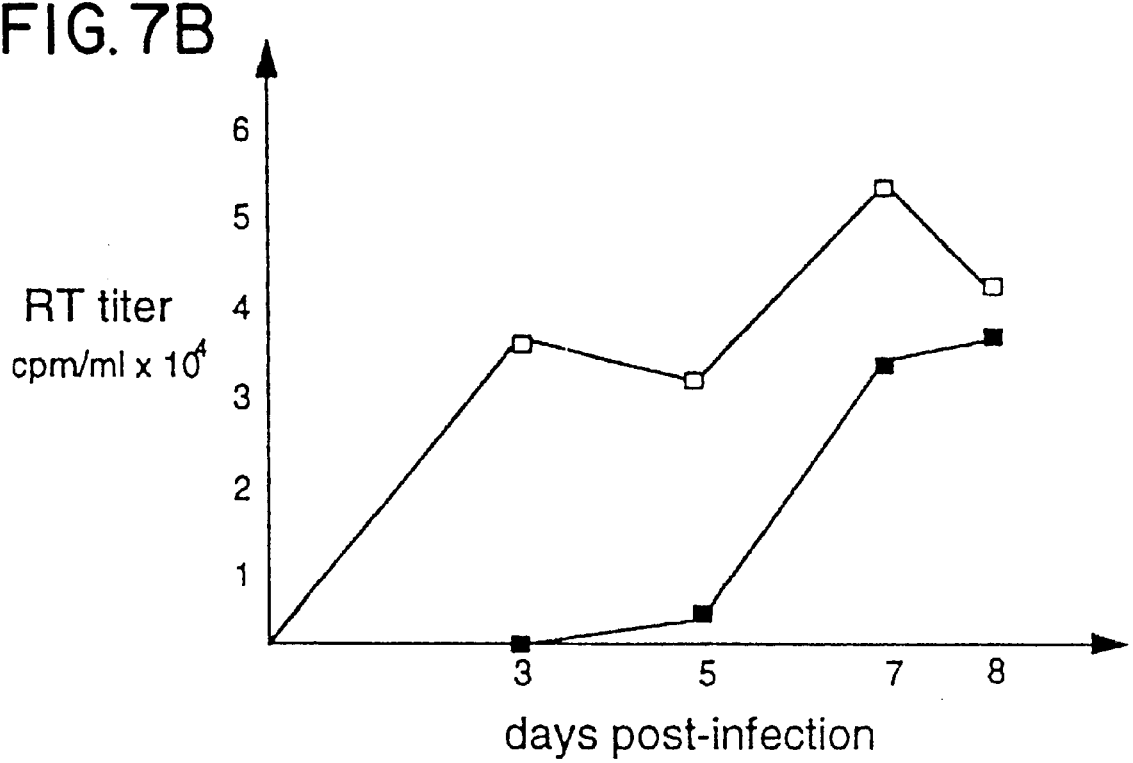

Vector pTIN502 (■) was delivered to U937 cells by one (FIG. 7A) or three (FIG. 7B) consecutive rounds of transduction. A similar population receiving pHIT111 was used to estimate the transduction frequency of a single round of transduction at 10–30% of the cells (data not shown). In addition, a control U937 population was transduced with vector pTIN414 (□). When multiple rounds of transduction were used, the cells were exposed to fresh retroviral vector stocks every forty-eight hours. Forty-eight hours after the final transduction, and in the absence of any drug selection, $2 \times 10^6$ cells of each of the TIN414 and TIN502-transduced populations were infected with 200 μl of an HIV-$1_{IIIB}$ viral stock at $5 \times 10^6$ $TCID_{50}$ per ml and viral spread was monitored over several days by analysing RT activity in the culture supernatant (FIG. 7). The TlN502-transduced populations were clearly protected relative to the control TIN414 populations (FIG. 7B) but this was dependent on multiple rounds of transduction as there was no protection of cells tranduced only once with TIN502. The lower levels of protection observed even in the multiply transduced TIN502 population compared with the selected TIN501 population (FIG. 6) were presumably due to the presence of non-transduced cells in the TIN502 population.

TABLE 1 pTIN414 is efficiently transduced by MLV packaging system.

| VECTOR | TARGET CELL | TITER (CFU/ML) |
|---|---|---|
| pHIT111 | NIH3T3 | $2 \times 10^5$ |
| pTIN414 |  | $8 \times 10^4$ |
| pHIT111 | HeLa | $6 \times 10^3$ |
| pTIN414 |  | $8 \times 10^3$ |

TABLE 2

TIN414 LacZ expression is Tat inducible.

| CELL LINE | RELATIVE B-GAL ACTIVITY (TWO EXPTS.) | | CELL LINE | RELATIVE B-GAL ACTIVITY (TWO EXPTS.) | |
|---|---|---|---|---|---|
| HeLa | 11 |  | NIH3T3 | 16 |  |
| HeLa111 | 34 | 42 | NIH3T3111 | 792 | 1776 |
| HeLa111 + Tat | 57 | 65 | NIH3T3111 + Tat | 1413 | 1729 |
| HeLa414 | 20 | 32 | NIH3T3414 | 146 | 105 |
| HeLa414 + Tat | 200 | 154 | NIH3T3414 + Tat | 179 | 279 |

REFERENCES

Adam, M. A., N. Ramesh, A. D. Miller and W. A. Osborne. (1991). J. Virol. 65:4985–4990.

Arya, S K., C. Guo, S. F. Josephs and F. Wong-Staal. (1985). Science 229:69–73.

Baltimore, D. (1988). Nature 335:395–396.

Berkhout, B. and K.-T. Jeang (1992). J. Virol. 66:139–149.

Bowtell, D. D. L., S. Cory, G. R. Johnson and T. J. Gonda. (1988). J. Virol. 62:2464–2473.

Brady, H., C. G. Miles, D. J. Pennington and E. A. Dzierzak. (1994). PNAS 91:365

Bushman, F. D. and R. Craigie. (1990). J. Virol. 64:5645–5648.

Cannon, P. M., W. Wilson, E. D. Byles, S. M. Kingsman, A. J. Kingsman. 1994. J. Virol. 68:4768–4775.

Caruso, M. and D. Klatzman. (1992). PNAS 89:182–186.

Cobrink, D., A. Aiyar, Z. Ge, M. Katzman, H. Huang and J. Leis. (1991). J. Virol 65:3864.

Cullen, B. R., P. T. Lomedico and G. Ju. (1984). Nature 307:241–245.

Emerman, M. and H. Temin. (1984). Cell 39:459–467.

Emerman, M. and H. Temin. (1986). Mol. Cell. Biol. 6:792–800.

Hantzopoulos P. A., B. A. Sullenger, G. Ungers and E. Gilboa. (1989). PNAS 86:3519–3523.

Higuchi, R. 1990. Recombinant PCR, p.177–183. In M. A. Innis, D. H. Gelfand, J. J. Sninsky and T. J. White (Eds.), PCR Protocols: Academic Press, San Diego.

Kadesch, T. and P. Berg (1986). Mol. Cell. Biol. 6:2593–2601.

Katz, R. A. and A. M. Skalka. (1994). Annu. Rev. Biochem. 63:133–173.

Kim, S., R. Byrn, J. Groopeman and D. Baltimore. (1989). J. Virol. 30 63:3708–3713.

Lehrman, S. (1994) Nature 371, 192

Liem, S. E., A. Ramezani, X. Li and S. Joshi. (1993). Hum. Gene Ther. 4:625–634.

Li, M., P. A. Hantzopoulos, D. Banerjee, S. C. Zhao, B. I. Schwiettzer, E.

Gilboa and J. R. Bertino. (1992). Hum. Gene Ther. 3:381–390.

Linial, M. L. and A. D. Miller. (1990). Ed. R. Swanstrom and P. K. Vogt. Springer-Verlag.

Liu, J., C. Woffendin, Z. Yang and G. J. Nabel. (1994). Gene Therapy 1:32–37.

Majors, J. (1990). Ed. R. Swanstrom and P. K. Vogt. Springer-Verlag.

Malim, M. H., S. Bohnlein, J. Hauber and B. R. Cullen (1989). Cell 58:205–214.

Mcivor, R. S., M. J. Johnson, A. D. Miller, S. Pitts, S. R. Williams, D. Valerio, D. W. Martin Jr. and I. M. Verna. (1987). Mol. Cell. Biol. 7:8380846.

Miller, A. D. and G. J. Rosman. (1989). Biotechniques 7:980–990.

Morgenstern, J. P., and H. Land. 1990. Nucl. Acids Res. 18:3587–3596.

Overell, R. W., K. E. Weisser and D. Cosman. (1988). Mol. cell. Biol. 8:1803–1808.

Page K. A., N. R. Landau, and D. R. Littman. 1990. J. Virol. 64:5270–5276.

Poznansky, M., A. Lever, L. Bergeron, W. Haseltine and J. Sodroski. (1991). J. Virol. 65:532.

Soneoka, Y., P. M. Cannon, E.E. Ramsdale. J. S. Griffiths, G. Romano, S. M. Kingsman and A. J. Kingsman. (1995). Nucl. Acids Res. 23:628–633.

Stuhiman, H., R. Jaaenisch and R. C. Mulligan (1989). Mol. Cell. Biol. 25 9:100–108.

Williams, D. A., S. H. Orkin and R. C. Mulligan. (1986). PNAS 83:2566–2570.

Xu, L., J. K. Lee, J. A. Wolff and T. Friedmann. (1989). Virology 171:331–341.

Yu, S.-F., T. von Ruden, P. W. Kantoff, C. Garber, M. Seiberg, U. Ruther, W. F. Anderson, E. F. Wagner and E. Gilboa. (1986). PNAS 83:3194–3198.

Yu, M., E. Poeschia and F. Wong-Staal. (1994). Gene Therapy 1:13–26.

What is claimed is:

1. A DNA construct comprising a packagable retroviral genome operably linked to a first promoter, wherein the retroviral genome comprises a 5' long terminal repeat (5' LTR) which includes sequences encoding R and U3 regions and 3' long terminal repeat (3' LTR) which includes sequences encoding R and U3 regions, and wherein at least said R regions of the 5' LTR and 3' LTR are identical to each other and are different from those of the retrovirus on which the retroviral genome is based.

2. A DNA construct according to claim 1, wherein the R regions of the 5' LTR and 3' LTR are obtained from a different retrovirus to the retrovirus on which the retroviral genome is based.

3. A DNA construct according to claim 1, wherein the R regions comprise a regulatory sequence heterologous to the retrovirus on which the retroviral genome is based.

4. A DNA construct according to claim 3, wherein the regulatory sequence is regulated by a regulatory factor from a different retrovirus to the retrovirus on which the retroviral genome is based.

5. A DNA construct according to claim 1, wherein part or all of the 3' LTR U3 region is obtained from a different retrovirus to the retrovirus on which the retroviral genome is based.

6. A DNA construct according to claim 5, wherein the 3' LTR U3 and R regions each comprises a regulatory sequence heterologous to the retrovirus on which the retroviral genome is based.

7. A DNA construct according to claim 6, wherein the regulatory sequence is regulated by a regulatory factor from a different retrovirus to the retrovirus on which the retroviral genome is based.

8. A DNA construct according to claim 5, wherein the 3' LTR U3 and R regions are obtained from a lentivirus.

9. A DNA construct according to claim 8, wherein the lentivirus is HIV.

10. A DNA construct according to claim 1, which further comprises a gene or genes between the 5' and 3' LTRs of the retroviral genome.

11. A DNA construct according to claim 1, wherein the retroviral genome is based on MLV.

12. A DNA construct according to claim 2, wherein the different retrovirus is HIV.

13. A DNA construct according to claim 1, further comprising within the retroviral genome an expression cassette comprising a constitutive or regulated promoter operably linked to a second gene.

14. A DNA construct according to claim 1, comprising within the retroviral genome a plurality of genes present in the same or different transcription units.

15. A DNA construct according to claim 1, wherein the first promoter is heterologous to the retroviral genome.

16. A DNA construct according to claim 9, wherein the first promoter is the CMV promoter.

17. A retroviral vector comprising a packagable retroviral genome operably linked to a first promoter, wherein the retroviral genome comprises a 5' long terminal repeat (5' LTR) which includes sequences encoding R and U3 regions and a 3' long terminal repeat (3' LTR) which includes sequences encoding R and U3 regions, and wherein at least said R regions of the 5' LTR and 3' LTR are identical to each other and are different from those of the retrovirus on which the retroviral genome is based.

18. A retroviral vector according to claim 17, wherein the R regions of the 5' LTR and 3' LTR are obtained from a different retrovirus to the retrovirus on which the retroviral genome is based.

19. A retroviral vector according to claim 17, wherein the R regions comprise a regulatory sequence heterologous to the retrovirus on which the retroviral genome is based.

20. A retroviral vector according to claim 19, wherein the regulatory sequence is regulated by a regulatory factor from a different retrovirus to the retrovirus on which the retroviral genome is based.

21. A retroviral vector according to claim 17, wherein part or all of the 3' LTR U3 regions is obtained from a different retrovirus to the retrovirus on which the retroviral genome is based.

22. A retroviral vector according to claim 21, wherein the 3' LTR U3 and R regions each comprises a regulatory sequence heterologous to the retrovirus on which the retroviral genome is based.

23. A retroviral vector according to claim 22, wherein the regulatory sequence is regulated by a regulatory factor from a different retrovirus to the retrovirus on which the retroviral genome is based.

24. A retroviral vector according to claim 23, wherein the 3' LTR U3 and R regions are obtained from a lentivirus.

25. A retroviral vector according to claim 24, wherein the lentivirus is HIV.

26. A retroviral vector according to claim 17, which further comprises a gene or genes between the 5' and 3' LTRs of the retroviral genome.

27. A retroviral vector according to claim 17, wherein the retroviral genome is based on MLV.

28. A retroviral vector according to claim 18, wherein the different retrovirus is HIV.

29. A retroviral vector according to claim 17, further comprising within the retroviral genome an expression cassette comprising a constitutive or regulated promoter operably linked to a second gene.

30. A retroviral vector according to claim 17, comprising within the retroviral genome a plurality of genes present in the same or different transcription units.

31. A retroviral vector according to claim 17, wherein the first promoter is heterologous to the retroviral genome.

32. A retroviral vector according to claim 26, wherein the first promoter is the CMV promoter.

33. A retroviral vector production system comprising a packaging cell line transfected with a DNA construct comprising a packagable retroviral genome operably linked to a first promoter, wherein said system produces a retroviral vector comprising the packagable retroviral genome, wherein the retroviral genome comprises a 5' long terminal repeat (5' LTR) which includes sequences encoding R and U3 regions and a 3' long terminal repeat (3' LTR) which includes sequences encoding R and U3 regions, and wherein at least said R regions of the 5' LTR and 3' LTR are identical to each other and are different from those of the retrovirus on which the retroviral genome is based.

34. A method of producing a packaged retrovirus which method comprises transfecting a packaging cell line with a DNA construct comprising a packagable retroviral genome operably linked to a first promoter, wherein said cell line produces a retroviral vector comprising the packagable retroviral genome and packages the vector, wherein the retroviral genome comprises a 5' long terminal repeat (5' LTR) which includes sequences encoding R and U3 regions and a 3' long terminal repeat (3' LTR) which includes sequences encoding R and U3 regions, and wherein at least said R regions of the 5' LTR and 3' LTR are identical to each other and are different from those of the retrovirus on which the retroviral genome is based.

35. A packaged retrovirus produced by the method of claim 34.

36. An isolated target cell infected or transduced with a retrovirus according to claim 35.

* * * * *